(12) United States Patent
Malo et al.

(10) Patent No.: US 6,544,782 B1
(45) Date of Patent: Apr. 8, 2003

(54) PREM: A POSITIVE SELECTION VECTOR SYSTEM FOR DIRECT PCR CLONING

(75) Inventors: Madhu Sudan Malo, Watertown, MA (US); Zaheed Husain, Medford, MA (US)

(73) Assignee: Synthegen Systems, Medford, MA (US)

( * ) Notice: Subject to any disclaimer, the term of this patent is extended or adjusted under 35 U.S.C. 154(b) by 0 days.

(21) Appl. No.: 09/710,726

(22) Filed: Nov. 13, 2000

(51) Int. Cl.[7] .......................... C12N 15/00; C07H 21/04
(52) U.S. Cl. .................................. 435/320.1; 536/24.33
(58) Field of Search ........................... 435/91.4, 320.1, 435/471; 536/24.33

(56) References Cited

U.S. PATENT DOCUMENTS

| | | | |
|---|---|---|---|
| 4,683,195 A | | 7/1987 | Mullis et al. .................. 435/6 |
| 4,683,202 A | | 7/1987 | Mullis ......................... 435/91 |
| 4,965,188 A | | 10/1990 | Mullis et al. .................. 435/6 |
| 5,487,993 A | | 1/1996 | Herrnstadt et al. ........ 435/172.3 |
| 5,824,469 A | | 10/1998 | Horwitz et al. ................ 435/6 |
| 5,856,144 A | | 1/1999 | Mierendorf et al. ....... 435/91.2 |
| 5,891,687 A | * | 4/1999 | Schlieper et al. .......... 435/91.4 |
| 5,910,438 A | | 6/1999 | Bernard et al. .......... 435/252.3 |
| 6,048,694 A | * | 4/2000 | Bramucci et al. .............. 435/6 |
| 6,127,171 A | * | 10/2000 | Slilaty et al. ............ 435/320.1 |
| 6,180,407 B1 | * | 1/2001 | Bernard et al. ............. 435/471 |

OTHER PUBLICATIONS

Pierce et al. A positive selection vector for cloning high molecular weight DNA by the bacteriophage P1 system: improved cloning eficacy. Proc.Natl.Acad.Sci.USA, vol. 89: 2056–2060, 1992.*

Ahn et al. Autoregulation of the gen encoding the replication terminator protein of *Bacillus subtillis*. Gene, vol. 132: 7–13, 1993.*

Stratagene Catalog. Gene characterization kits. Stratagene Catalog. p. 39, 1988.*

Messing et al.; "Filamentous Coliphage M13 as a Cloning Vehicle: Insertion of a Hind II Fragment of the Lac Regulatory Region in M13 Replicative Form in Vitro", Proc. Natl. Acad. Sci. USA, 74(9): 3642–3646, (Sep. 1977).

Norrander et al.; "Construction of Improved M13 Vectors Using Oligodeoxynucleotide–directed Mutagenesis", Gene, 26: 101–106, (1983).

Yanisch–Perron et al.; "Improved M13 Phage Cloning Vectors and Host Strains: Nucleotide Sequences of the M13mp18 and pUC19 Vectors", Gene 33: 103–119, (1985).

Malo and Loughlin; "Promoter– detection Vectors For *Escherichia coli* with Multiple Useful Features", Gene, 64:207–215, (1988).

Pierce, et al; "A positive selection vector for cloning high molecular weight DNAby the bacteriophage P1 system: Improved cloning efficacy", Proc. Natl. Acad. Sci. USA, 89: 2056–2060, (Mar. 1992).

Trudel et al; "pGATA: A Positive Selection Vecotr Based on the Toxicity of the Transcription Factor GATA–1 to Bacteria", BioTechniques, 20:684–693 (Apr. 1996).

Bolivar et al.; "Construction and Characterization of New Cloning Vehicles", Gene, 2: 95–113, (1977).

Robben, J., et al.; Insertional re–activation of a chloramphenicol acetyltranferase misfolding mutant protein, *Protein Engineering*, vol. 8 No. 2, pp 159–165, 1995.

* cited by examiner

*Primary Examiner*—Jeffrey Fredman
*Assistant Examiner*—Suryaprabha Chunduru
(74) *Attorney, Agent, or Firm*—Ropes & Gray (57) ABSTRACT

The present invention describes the development of a positive selection vector based on regulatory element modulation, wherein such modulation is achieved via insertional reconstruction or destruction of a regulatory element controlling transcription, translation, DNA replication and termination. A positive selection cloning vector pREM5Tc has been developed based on insertional reconstruction of a regulatory element of a reporter gene. The vector pREM5Tc carries the tetracycline resistance reporter gene with no functional –35 region of its promoter, a regulatory element, thus resulting in no expression of the tetracycline resistance gene. Hence a host cell carrying the vector pREM5Tc is unable to produce the tetracycline resistance gene protein resulting in inhibition of its growth in presence of tetracycline. An *E. coli* consensus –35 region is recognized as 5'-TTGACA-3' and a primer used in polymerase chain reaction (PCR) carries at its 5' end the sequence 5'-TGTCAA-3', which is the complementary sequence of 5'-TTGACA-3'. The PCR-amplified DNA fragment is ligated to pREM5Tc thus reconstructing the functional promoter of the tetracycline resistance reporter gene. Subsequent transformation of a host cell with the recombinant vector (carrying an insert DNA) results in production of the tetracycline resistance reporter gene protein that confers resistance to tetracycline thus allowing only the recombinants to grow in presence of tetracycline. The positive selection vector pREM5Tc greatly reduces, if not eliminates, the number of exonuclease-generated false positive clones.

22 Claims, 4 Drawing Sheets

```
                                          Afl II
5'-TTG AAT ACT CAT ACT CTT CCT TAA GCA ACA CCA CCG AAC CAT TAT ACG
3'-AAC TTA TGA GTA TGA GAA GGA ATT CGT TGT GGT GGC TTG GTA ATA TGC
       ←——— ApR         RBS

Sac II                        Sfi I/Not I              -35* TcR
   AAA CCG CGG AAA TTA TAA AGG CCA AAG CGG CCG CTG TCA AAC CCG GGA
   TTT GGC GCC TTT AAT ATT TCC GGT TTC GCC GGC GAC AGT TTG GGC CCT
            -10 ApR                                 -35 ApR      Sma I

-10 TcR                              Sfi I/Not I
   ACA AGA AGA CAA ATA TAA TAC TAT AGT GAG TCG TAT TAG GCC AAA GCG
   TGT TCT TCT GTT TAT ATT ATG ATA TCA CTC AGC ATA ATC CGG TTT CGC
                                ←——————— T7 promoter Sac I                         RBS          TcR ——→
   GCC GCG AGC TCA CAG ACC ACA GCC AAA GGA ACC GAC CAT GAA ATC TAA-3'
   CGG CGC TCG AGT GTC TGG TGT CGG TTT CCT TGG CTG GTA CTT TAG ATT-5'
```

PREM: A POSITIVE SELECTION VECTOR SYSTEM FOR DIRECT PCR CLONING

CROSS-REFERENCE TO RELATED APPLICATIONS

| References Cited [Referenced By] U.S. Pat. Documents | | | |
| --- | --- | --- | --- |
| 4683195 | July, 1987 | Mullis et al. | 435/6 |
| 4683202 | July, 1987 | Mullis | 435/91 |
| 4965188 | Oct., 1990 | Mullis et al. | 435/6 |
| 5487993 | Jan., 1996 | Herrnstadt et al. | 435/172 |
| 5856144 | Jan., 1999 | Mierendorf et al. | 435/91 |
| 5891687 | April, 1999 | Schlieper et al. | 935/172 |
| 5910438 | June, 1999 | Bernard et al. | 435/252 |

OTHER REFERENCES

Ahrenhotz et al., "A conditional suicide system in *Escherichia coli* based on intracellular degradation of DNA" Appl. Environ. Microbiol. 60,3746–3751(1994).

Altenbuchner et al., "Positive selection vectors based on palindromic DNA sequences" Methods Enzymol. 216, 457–466 (1992).

Balbas et al., "Plasmid vector pBR322 and its special-purpose derivatives—a review" Gene 50, 3–40 (1986).

Bernard et al., "New ccdB positive-selection cloning vectors with kanamycin or chloramphenicol selectable markers" Gene 148, 71–74 (1994).

Bolivar et al., "Construction and characterization of new cloning vehicles, II. A multipurpose cloning system" Gene 2, 95–113 (1977).

Burns D. M. and Beacham, I. R., "Positive selection vectors: a small plasmid-vector useful for the direct selection of Sau3A-generated overlapping DNA fragments" Gene 27, 323–325 (1984).

Clark, J. M., "Novel non-templated nucleotide addition reactions catalyzed by prokaryotic and eukaryotic DNA polymerases" Nucl. Acids Res. 16, 9677–9686 (1988).

Debarbouille, M. and Raibaud, O, "Expression of the *Escherichia coli* malPQ operon remains unaffected after drastic alteration of its promoter" J. Bacteriol. 153, 1221–1227 (1983).

Harrley, C. B. and Reynolds, R. P., "Analysis of *E. coli* promoter sequences" Nucl. Acids Res. 15, 2343–2361 (1978).

Henrich, B. and Plapp, R., "Use of the lysis gene of bacteriophage phi X174 for the construction of a positive selection vector" Gene 42, 345–349 (1986).

Henrich, B. and Schmidtberger, B., "Positive-selection vector with enhanced lytic potential based on a variant of phi X174 phage gene E" Gene 154, 51–54 (1995).

Holton, T. A. and Graham, M. W., "A simple and efficient method for direct cloning of PCR products using ddT-tailed vectors" Nucl. Acids Res. 19, 1156 (1991).

Hu, G., "DNA polymerase-catalyzed addition of nontemplated extra nucleotides to the 3' end of a DNA fragment" DNA Cell Biol. 12, 763–770 (1993).

Kast, P., "pKSS—a second-generation general purpose cloning vector for efficient positive selection of recombinant clones" Gene 138, 109–114 (1994).

Kaufmann, D. L. and Evans, G. A., "restriction endonuclease cleavage at the termini of PCR products" BioTechniques 9, 304–306 (1990).

Kuhn et al., "Positive selection vectors utilizing lethality of EcoRI endonuclease" Gene 42, 252–263 (1986).

Malo, M. S. and Loughlin, R. E., "Promoter elements and regulation of expression of the cysD gene of *Escherichia coli* K-12" Gene 87, 127–131 (1990).

Mead et al., "Bst DNA polymerase permits rapid sequence analysis from nanogram amounts of template" BioTechniques 9, 657–663 (1991).

Messing et al., "Filamentous coliphage M13 as a cloning vehicle: insertion of a HindII fragment of the lac regulatory region in M13 replicative form in vitro" Proc. Natl. Acad. Sci. 79, 3642–3646 (1977).

Mullis, K. B. and Faloona, F. A., "Specific synthesis of DNA in vitro via polymerase-catalyzed chain reaction" 1987, Methods Enzymol. 155, 335–350 (1987).

Norrander et al., "Construction of improved M13 vectors using oligodeoxynucleotide-directed mutagenesis" Gene 26, 101–106 (1983).

Pierce et al., "A positive selection vector for cloning high molecular DNA by bacteriophage P1 system: improved cloning efficiency" Proc. Natl. Acad. Sci. 89, 2056–2060 (1992).

Reznikoff et al., "The regulation of transcription initiation in bacteria" Annu. Rev Genet. 19, 355–387 (1985).

Sambrook et al., Molecular Cloning: A Laboratory Manual, Cold Spring Harbor Laboratory, Cold Spring Harbor, N.Y. (1989).

Saiki et al., "Enzymatic amplification of beta-globin genomic sequences and restriction site analysis for diagnosis of sickle cell anemia" Science 230, 1350–1354 (1985).

Yanisch-Perron et al., "Improved M13 phage cloning vectors and host strains: nucleotide sequences of the M13mp18 pUC19 vectors" Gene 33, 103–119 (1985).

Yazynin et al., "A plasmid vector with positive selection and directional cloning based on a conditionally lethal gene" Gene 169, 131–132 (1996).

FIELD OF THE INVENTION

The present invention relates to positive selection vectors for direct cloning of PCR-amplified nucleic acids. The invention also deals with modulation of regulatory elements for developing such vectors. The invention greatly reduces, if not eliminates, exonuclease-induced false positive clones in a DNA cloning experiment.

BACKGROUND OF THE INVENTION

Recent advances in the field of molecular biology and genetic engineering include polymerase chain reaction or PCR as described in U.S. Pat. Nos. 4,683,195, 4,683,202 and 4,965,188. To amplify or reproduce copies of a targeted nucleic acid, PCR uses a polymerase, targeted sequence-specific forward and reverse primers, deoxynucleotides and a minute amount of target nucleic acid as the template. Exponential amplification of the targeted DNA sequence is achieved by repeated cycles of denaturation of double-stranded DNA followed by primer annealing and primer extension.

PCR-amplified DNA itself has been used for diagnosis, quantitation of the template DNA, direct sequencing and several other applications (U.S. Pat. Nos. 5,856,144; 5,487,993 and 5,891,687). However, for applications such as detection of polymorphism, mutations, sequencing, expression of genes, synthesis of RNA probes etc., it is often necessary to obtain a large quantity of DNA. This necessitates isolation of a bacterial clone carrying the PCR-generated targeted DNA fragment in a vector. Various strategies have been described for cloning PCR-generated DNA fragments into appropriate vectors. One such method involves incorporation of restriction endonuclease cleavage sites near the 5' end of the PCR primers. The PCR product thus obtained is subjected to purification, restriction digestion with the respective endonuclease followed by ligation into a compatible vector, transformation and identification of the bacterial clone carrying the PCR fragment (Kaufmann and Evans, 1990, BioTechniques 9, 304–306).

The most commonly used strategy involves the nontemplate-dependent terminal transferase or extendase activity of Taq DNA polymerase, which usually produces a dAMP (deoxyadenosine monophosphate) overhang at the 3' end of the PCR-amplified DNA fragment (Clark, 1988, Nucl. Acid Res. 16, 9677–9686; Hu, 1993, DNA Cell Biol. 12, 763–770). The PCR product thus obtained is ligated into a linearized vector carrying a dTMP (deoxythymidine monophosphate) overhang at the 3' end (U.S. Pat. No. 5,487,993; Mead et al., 1991, BioTechniques 9, 657–663; Holton and Graham, 1991, Nucl. Acids Res. 19, 1156). In a similar strategy, Taq DNA polymerase generated PCR fragments carrying dAMP overhang at the 3' end are ligated into a linearized vector carrying an inosine or uracil overhang at the 3' end (U.S. Pat. No. 5,856,144).

Since the above-mentioned vectors lack the positive selection capability, upon transformation, all host cells carrying either the recombinant vector (containing an insert) or the non-recombinant vector (containing no insert) grow in the desired medium at an equal growth rate. To differentiate between a host cell carrying the non-recombinant religated vector from the host cell carrying the recombinant vector, the DNA fragment to be cloned is usually inserted into a chromogenic gene, the product of which is thus inactivated rendering the recombinant colony white in a chromogenic medium. When the chromogenic gene is lacZ, the transformant carrying the non-recombinant vector turns blue in the presence of X-gal, the substrate for the lacZ gene product β-galactosidase (Messing et al., 1977, Proc. Natl. Acad. Sci. 79, 3642–3646; Norrander et al., 1983, Gene 26, 101–106; Yanisch-Perron et al., 1985, Gene 33, 103–119). When the number of recombinant colonies are low and non-recombinant colonies are high in a plate, then it becomes very difficult to differentiate the recombinant colonies from the non-recombinant colonies. High number of colonies on a plate also lead to contamination between the recombinant and non-recombinant colonies.

To ameliorate the problems associated with the chromogenic selection of recombinant clones many vectors have been developed with positive selection capability allowing only the recombinant clone to grow in a selection medium. Most of these positive selection vectors have been developed based on insertional inactivation of lethal genes (Burns and Beacham, 1984, Gene 27, 323–325; Balbas et al., 1986, Gene 50, 3–40; Pierce et al., 1992, Proc. Natl. Acad. Sci. 89, 2056–2060; Henrich and Plapp, 1986, Gene 42, 345–349; Henrich and Schmidtberger, 1995, Gene 154, 51–54; Bernard et al., 1994, Gene 148, 71–74; Kuhn et al., 1986, Gene 42, 253–263; U.S. Pat. Nos. 5,910,438; 5,891,687). A vector system based on abolition of sensitivity towards metabolite has also been described (Kast, 1994, Gene 138,109–114). Vectors have also been constructed based on selection by means of DNA-degrading or RNA-degrading enzymes (Yaznin et al., 1996, Gene 169, 131–132; Ahrenhotz et al., 1994, Appl. Environ. Microbiol. 60, 3746–3751) as well as based on selection by destruction of long palindromic DNA sequences (Altenbuchner et al., 1992, Methods Enzymol. 216, 457–466).

The presently available positive selection vectors as well as other cloning vectors have several disadvantages. An inherent problem of a vector with a lethal or a chromogenic gene is a high number of false positive clones, i.e., clones without any insert. The false positive clones could arise as revertants following mutations in the lethal or chromogenic gene rendering it inactive. False positive clones may also arise from transformation of linearized vectors, which may get deleted and subsequently recircularized inside the host cell thus inactivating the lacZ or the lethal gene. However, the biggest disadvantage of every cloning system available today is the generation of exonuclease-induced false positive clones. The reagents used in restriction digestion, PCR and ligation, particularly restriction enzymes, polymerases and ligases, are usually contaminated with exonucleases, which may not be completely removed from larger lots of commercial preparations. Exonuclease digestion deletes some nucleotide bases from the cloning site in the chromogenic or lethal gene in a linearized vector DNA. Thus recirculariza­tion of such vectors result in inactivation of the chromogenic or lethal genes, and upon transformation these vectors give false positive transformant clones. Similarly, a palindromic sequence could also be destroyed by exonuclease digestion, thus giving false positive clones.

When a small DNA fragment is inserted in frame with the nucleotide sequence of the lethal gene or the chromogenic gene, then the function of the lethal or chromogenic gene may not be altered, thus making it impossible to clone such small DNA fragments. Furthermore, when cloning of a small DNA fragment results in only diminished function of the lethal gene, then clones grow at a reduced rate in case of positive selection vectors. These clones could be confused with the non-recombinant clones growing because of diminished selection pressure due to, for example, long period of incubation.

A further disadvantage of the vectors based on lethal genes is that sometimes a complex medium is required to activate the selection mechanism (Kast, 1994, Gene 138, 109–114). Also, the positive selection vectors carrying lethal or chromogenic genes require special host cells for transformation, e.g., CcdB based vectors require F⁻ host cells (U.S. Pat. No. 5,910,438), CAP based vectors require adenyl-cyclase positive host cells (U.S. Pat. No. 5,891,687) and lacZ based vectors require lac⁻ host cells (Messing et al., 1977, Proc. Natl. Acad. Sci. 79, 3642–3646; Norrander et al., 1983, Gene 26, 101–106; Yanisch-Perron et al., 1985, Gene 33, 103–119). A special regulatory system, usually lacI or CI repressor system (U.S. Pat. No. 5,910,438; Pierce et al., 1992, Proc. Natl. Acad. Sci. 89, 2056–2060), has also to be in place preventing the expression of the lethal gene in the host cell used for large scale preparation of the vector DNA.

OBJECTS OF THE INVENTION

The object of the present invention is to develop a simple cloning and/or a sequencing vector which should have the capability of positive selection allowing only the recombinant clones (carrying an insert DNA) to grow in a selection medium, whereas, the non-recombinant clones (carrying no insert) will not grow. A major object of the present invention is to eliminate or greatly reduce the false positive clones associated with all the presently available cloning systems. Especial emphasis is placed on the elimination of exonuclease-induced false positive clones. Thus it is aimed to apply the principle of modulation of a regulatory element, which involves insertional reconstruction of a regulatory element controlling transcription, translation, DNA replication and termination. It was decided to develop a positive selection vector based on insertional reconstruction of a regulatory element of an antibiotic resistance reporter gene lacking the said regulatory element. When the reporter gene is an antibiotic resistance gene, after reconstruction of its regulatory element, upon transformation of a host cell the antibiotic resistance reporter gene is expressed thus allowing only the clones making the antibiotic resistance reporter protein to grow in a specific selection medium containing the respective antibiotic.

Use of the principle of reconstruction of a regulatory element should also greatly reduce, if not eliminate, revertants because firstly, probability of spontaneous mutational creation of a regulatory element is minimal, and secondly, any spontaneous mutation in the coding sequence of an antibiotic resistance reporter gene would most probably destroy the function of the reporter gene protein resulting in inhibition of the growth of the host cell in the selection medium containing the respective antibiotic.

A vector system based on antibiotic resistance gene as the reporter gene should also eliminate the need for any special type of host cells.

Elimination of the disadvantages associated with presently available vectors is a desirable objective, and hence the present invention will be a substantial technological achievement.

SUMMARY OF THE INVENTION

The present invention describes a strategy for developing positive selection vectors based on regulatory element modulation, wherein such modulation is achieved via reconstruction or destruction of a regulatory element controlling transcription, translation, DNA replication and termination. The invention also describes the use of such vectors for direct cloning of PCR products. As an example of application of the strategy a positive selection vector pREM5Tc has been developed based on reconstruction of a regulatory element of a reporter gene. The vector pREM5Tc carries a functionally inactive mutant −35 region of the *E. coli* promoter, a transcriptional regulatory element. The −35 region of the tetracycline resistance gene promoter has been changed to 5'-AAACCC-3', whereas, the consensus −35 region of an *E. coli* promoter is 5'-TTGACA-3', and is situated 17+/−1 basepairs (bp) upstream of the −10 region of a promoter (Harrley and Renolds, 1987, Nucl. Acid Res. 15, 2343–2361). Even though the −10 region of the tetracycline resistance gene promoter in pREM5Tc has been converted into a consensus one of 5'-TATAAT-3' (Harrley and Renolds, 1987, Nucl. Acid Res. 15, 2343–2361) the above change in the −35 region of the promoter stops transcription from this promoter, and as a result the vector upon transformation of a host cell is unable to produce tetracycline resistance gene protein, and hence cannot confer resistance to tetracycline and does not grow in a medium containing tetracycline. A unique cloning site Sma I (5'-CCCGGG-3') has been created, and the axis of symmetry of this palindrome (5'-CCCGGG-3') is located just 17 bp upstream of the −10 region (5--TATAAT-3') of the tetracycline resistance gene promoter. Upon Sma I restriction cleavage blunt-ended linearized vector is generated, and hence if any DNA fragment carrying 5'-TTGACA-3' at its 3' end is inserted in this position, the −35 region of the tetracycline resistance gene promoter is reconstructed resulting in a recombinant plasmid which upon transformation should confer resistance to tetracycline.

A PCR primer carrying the nucleotides 5'-TGTCAA-3' at its 5' end is used in PCR. The resulting blunt-ended PCR products thus obtained would carry 5'-TTGACA-3' at the 3' end of the strand complementary to the primer. Ligation of this PCR product into the above-mentioned Sma I digested vector reconstructs the −35 region of 5'-TTGACA-3', which works as a functional −35 region when the recombinant vector transforms a host cell thus expressing the tetracycline resistance gene and conferring resistance to tetracycline. This also ensures unidirectional cloning of the insert.

The upstream region of the −35 region of tetracycline resistance gene in this vector has been changed so that it should not reconstruct a functional −35 region even upon exonuclease digestion without destroying the regulatory elements of the selectable marker ampicillin resistance gene. Thus this cloning system greatly reduces false positive clones induced by exonuclease digestion. The region between the start codons of ampicillin and tetracycline resistance genes has also been modified such that it does not carry any other consensus −10 region for the tetracycline resistance gene, except the recognized consensus −10 region situated 14 bp downstream of the Sma I cloning site.

In between the start codons for the tetracycline and ampicillin resistance genes some restriction sites, e.g., Sac I, Sac II, Not I and Sfi I sites, have been introduced for an easy extraction of the insert DNA fragment.

BRIEF DESCRIPTION OF FIGURES

FIG. 4 shows the pREM5Tc DNA sequence between the start codons for ampicillin and tetracycline resistance genes. The asterisk indicates mutations in the −35 region of the promoter of tetracycline resistance gene.

DETAILED DESCRIPTION OF THE INVENTION

The present invention is directed to construct a positive selection vector system based on modulation of a regulatory element controlling transcription, translation, DNA replication and termination. The modulation of a regulatory element is accomplished by insertional reconstruction or destruction of the regulatory element. The invention also describes the use of such a vector for direct or indirect cloning of PCR-generated DNA fragments. The vector carries a viral or a plasmid origin for autonomous replication in an appropriate host cell. The vector may be a phagmid, when the vector carries a plasmid origin of replication as well as an M13 or an f1 origin of replication for easy production of single-stranded DNA upon infection with a helper phage. The vector also carries a selectable marker gene, a reporter gene and/or a regulatory gene, and a cloning site for inserting the PCR-amplified DNA fragments or the restriction DNA fragments. The vector developed based on insertional reconstruction of a regulatory element carries a functionally inactive mutated regulatory element, whereas the vector developed based on destruction of a regulatory element carries a functionally active regulatory element. Furthermore, the vector may carry a phage promoter around the cloning site for easy in vitro production of RNA probes.

The invention contemplates development of chromogenic or fluorogenic selection vectors based on modulation of the regulatory elements of lacZ or fluorescent protein genes.

The selectable marker gene, which allows contamination-free growth of the host cells harboring the vector, is usually an antibiotic gene, however, it could be an essential gene for the host or the vector itself A chromogenic gene, such as, lacZ or GFP (Green Fluorescent Protein) gene can also serve as a selectable marker gene.

The vector carries a reporter gene, the function of which could easily be assayed either qualitatively or quantitatively. The reporter gene could be an antibiotic resistance gene, a toxic gene, an essential gene for the host or the vector, and also chromogenic and fluorogenic genes, such as lacZ and GFP genes.

A gene could be regulated at the level of transcription or translation. The transcriptional regulatory elements encompass promoters, operators, terminators, enhancers, transcription factor binding sites, positive regulatory protein (activator) binding sites, negative regulatory protein (repressor) binding sites, splicing junctions etc The space between two defined regulatory elements is also involved in regulation and is thus considered as a regulatory element, especially the spacer region in between the −10 and −35 regions of the E. coli promoter as elaborated below.

Translational regulatory elements are ribosome binding sites, start and stop codons, and 5' and 3' untranslational regions of a transcript involved in translational regulation.

DNA replication and termination regulatory elements encompasses DNA sequences, such as origin of replication (ori), autonomously replicative sequence (ARS), replication bubble (eye), fork structure and chromosomal replication terminator etc.

The most extensively studied regulatory element is the E. coli promoter, which is recognized by E. coli RNA polymerase holoenzyme to initiate transcription (Harrley and Renolds, 1987, Nucl. Acid Res. 15, 2343–2361). The E. coli promoter consists of two regions of hexanucleotides located about 10 and 35 basepairs upstream of the transcription start site; and these regions are designated as the −10 and −35 regions of the E. coli promoters (Harrley and Renolds, 1987, Nucl. Acid Res. 15, 2343–2361). Analysis of large number of E. coli promoters established that the sequences 5'-TATAAT-3' and 5'-TTGACA-3' are the consensus sequences for the −10 and −35 regions respectively (Harrley and Renolds, 1987, Nucl. Acid Res. 15, 2343–2361). Mutations that enhance the similarity of a promoter to these consensus sequences (by changing the −10 and/or −35 regions) enhance the promoter activity, whereas, any mutation causing deviation from these consensus sequences diminishes the promoter activity (Reznikoff et al., 1985, Annu. Rev. Genet. 19, 355–387; Malo and Loughlin, 1990, Gene, 87, 127–131). The spacing between the −10 and −35 regions is 17+/−1 basepairs, and alteration of this spacing affects gene expression (Debarbouille and Raibaud, 1983, J. Bacteriol. 153, 1221–1227; Reznikoff et al., 1985, Annu. Rev. Genet. 19, 355–387).

A regulatory element is functionally inactive in case of a vector developed based on insertional reconstruction of the regulatory element of a reporter gene or of a regulatory gene controlling the expression of the reporter gene. Thus upon transformation of a host cell the vector is unable to produce any reporter gene protein or the regulatory gene protein respectively. When the reporter gene is an antibiotic resistance gene and the vector is developed based on reconstruction of the regulatory element of the reporter gene, the vector cannot produce the antibiotic resistance reporter gene protein resulting in inhibition of the growth of host cell in a specific selection medium containing the respective antibiotic. Only insertional reconstruction of the regulatory element will ensure production of the antibiotic resistance reporter gene protein thus allowing a host cell harboring the recombinant vector (carrying an insert DNA) to grow in a selection media containing the respective antibiotic.

A positive selection vector can be developed based on insertional reconstruction of a regulatory element of a regulatory gene controlling the expression of a reporter gene. A vector can carry a reporter gene under the control of a positively regulated promoter, for example the cysD promoter, or under the control of a negatively regulated promoter, for example, the lac promoter. The cysD promoter in E. coli is positively regulated by the positive regulatory (activator) CysB protein, which means binding of CysB protein to the cysD promoter initiates transcription from the cysD promoter. The lac promoter for lacZYA operon in E. coli is negatively controlled by the negative regulatory (repressor) LacI protein, which means binding of the LacI protein to the lac operator stops transcription from the lac promoter. Different combinations of regulatory genes and reporter genes could be used to develop multiple positive selection vectors. A positive selection vector could be developed carrying an antibiotic resistance reporter gene under the control of cysD promoter, and the cysB gene as the regulatory gene, wherein the cysB gene lacks a functional regulatory element. Only insertional reconstruction of the cysB regulatory element will allow production of the antibiotic resistance reporter gene protein resulting in growth of only a host cell harboring a recombinant (carrying an insert DNA) clone in presence of the respective antibiotic. Similarly, a positive selection vector could be developed carrying a toxic reporter gene, e.g., ccdB gene, under the control of lac promoter, and the lacI gene as the regulatory gene, wherein the lacI gene lacks a functional regulatory element. Only insertional reconstruction of the lacI regulatory element will inhibit production of the toxic gene protein resulting in growth of only a host cell harboring a recombinant (carrying an insert DNA) clone in a specific medium.

Chromogenic or fluorogenic selection vectors can also developed based on reconstruction of a regulatory element of a reporter gene or of a regulatory gene controlling the expression of the reporter gene. Insertional reconstruction of a regulatory element leading to production of LacZ or fluorescent proteins (e.g., GFP) would result in a chromogenic or fluorogenic selection vector.

Insertional reconstruction of a regulatory element controlling DNA replication and termination could also be used to develop a positive selection vector.

A regulatory element is functionally active in a vector developed based on destruction of a regulatory element of a reporter gene or of a gene controlling the expression of the reporter gene. When a vector carries a toxic gene, for example ccdb gene as its reporter gene, then insertional destruction of its regulatory elements stops production of the toxic gene protein and thus a host cell harboring a recombinant clone (carrying an insert DNA) grows in a specific medium.

A positive selection vector can be developed based on insertional destruction of a regulatory element of a regulatory gene controlling the expression of a reporter gene. A vector can carry a reporter gene under the control of a positively regulated promoter, for example the cysD promoter, or under the control of a negatively regulated promoter, for example, the lac promoter. The cysD promoter in E. coli is positively regulated by the positive regulatory (activator) CysB protein, which means binding of CysB protein to the cysD promoter initiates transcription from the cysD promoter. The lac promoter for lacZYA operon in E. coli is negatively controlled by the negative regulatory (repressor) LacI protein, which means binding of the LacI protein to the lac operator stops transcription from the lac promoter. Different combinations of regulatory genes and reporter genes could be used to develop multiple positive selection vectors. A positive selection vector could be developed carrying an antibiotic resistance reporter gene under the control of lac promoter, and the lacI gene as the regulatory gene, wherein the lacI gene carries the functional regulatory elements and as a result stops transcription from the lac promoter controlling the expression of the antibiotic resistance reporter gene. Insertional destruction of the lacI regulatory elements will allow production of the antibiotic resistance reporter gene protein resulting in growth of only a host cell harboring a recombinant (carrying an insert DNA) clone in presence of the respective antibiotic. Similarly, a positive selection vector could be developed carrying a toxic reporter gene, e.g., ccdB gene, under the control of cysD promoter, and the cysB gene as the regulatory gene, wherein the cysB gene carries all functional regulatory elements and as result allows expression of the toxic gene from the cysD promoter. Insertional destruction of a cysB regulatory element will inhibit production of the toxic gene protein resulting in growth of only a host cell harboring a recombinant clone (carrying an insert DNA) in a specific medium. Similarly, instead of destruction of a regulatory element, insertional destruction of a regulatory gene could also be used to develop a positive selection vector.

Chromogenic or fluorogenic selection vectors can also developed based on destruction of a regulatory element of a reporter gene or of a regulatory gene controlling the expression of the reporter gene. Insertional destruction of a regulatory element leading to inhibition of production of LacZ or fluorescent proteins (e.g., GFP) would result in a chromogenic or fluorogenic selection vector.

Insertional destruction of a regulatory element controlling DNA replication and termination could also be used to develop a positive selection vector.

A positive selection vector pREM5Tc has been developed based on reconstruction of the −35 region of the tetracycline resistance gene promoter. In this vector the −35 region of the tetracycline resistance gene promoter has been changed such that it is no longer recognized by E. coli RNA polymerase resulting in no expression of the tetracycline resistance gene. As a result any host cell harboring the vector is unable to produce tetracycline resistance gene protein, and hence is unable to grow in presence of tetracycline. When a PCR fragment carrying 5'-TTGACA-3' at its 3' end is inserted in the unique Sma I cloning site in this vector, the −35 region is reconstructed. Upon transformation the host cell carrying the recombinant clone expresses tetracycline resistance gene thus allowing the cells to grow in presence of tetracycline. The vector has been successfully used to clone PCR fragments amplified by Pfu and Taq DNA polymerases.

EXAMPLE 1

General Techniques of Molecular Biology

Unless otherwise indicated, the molecular biology techniques related to this invention are described in Sambrook et al., Molecular Cloning: A Laboratory Manual, Cold Spring Harbor Laboratory, Cold Spring Harbor, N.Y., 1989.

PCR was performed for enzymatic amplification of a targeted DNA fragment (Saiki et al., 1985, Science 230, 1350–1354; Mullis and Faloona, 1987, Method Enzymol. 155, 335–350) using a DNA thermal cycler (Perkin Elmer Cetus, Foster City, Calif., USA) according to the manufacturer's instructions. The thermostable DNA polymerases and the PCR kit were used according to the recommendations of the respective suppliers (Perkin Elmer Cetus, Foster City, Calif., USA; Stratagene, La Jolla, Calif., USA).

The restriction endonuclease cleavage of DNA was performed according to the specifications of the manufacturers (New England Biolabs, Beverly, Mass., USA; Stratagene, La Jolla, Calif., USA). After restriction digestion, the restriction endonuclease was inactivated by heat treatment or by phenol:chloroform:isoamyl alcohol (25:24:1) treatment followed by ethanol precipitation of DNA. The precipitated DNA was then pelleted by centrifugation and the pellet was dried in air.

DNA ligation was achieved by incubating the DNA (vector and/or insert) in presence of T4 DNA ligase according to the instructions of the manufacturer (Life Technologies/GIBCO-BRL, Rockville, Md., USA).

Transformations of the commercially available competent host cells were carried out as per the instructions of the supplier (Life Technologies/GIBCO-BRL, Rockville, Md., USA). The transformants were plated onto LB agar medium (Life Technologies/GIBCO-BRL, Rockville, Md., USA) containing ampicillin (100 μg/ml; Sigma, St. Louis, Mo., USA) and/or tetracycline (12.5 μg/ml; Sigma, St. Louis, Mo., USA). For small or large scale preparation of transformant plasmid DNA, LB broth (Life Science Technologies/ GIBCO-BRL, Rockville, Md., USA) containing ampicillin (100 μg/ml) and/or tetracycline (12.5 μg/ml) was used. Plasmid DNA was isolated using alkaline lysis method.

Plasmids pBR322 (Bolivar et al., 1977, Gene 2, 95–113) and pUC19 (Norrander et al., 1983, Gene 26, 101–106) DNA were purchased from New England Biolabs (Beverly, Mass., USA). Plasmid pUC119 (Vieira and Messing, 1987, Methods Enzymol. 153, 3–11) was obtained from Bayou Biolabs (Harahan, La., USA). E. coli DNA was obtained from Sigma (St. Louis, Mo., USA). Restriction endonucleases were purchased from New England Biolabs (Beverly, Mass., USA). Taq DNA polymerase and dNTPs were obtained from Perkin Elmer (Foster City, Calif., USA), and T4 DNA ligase was obtained from Life Technologies/ GIBCO-BRL (Rockville, Md., USA). Pfu and Taqplus DNA polymerases were purchased from Stratagene (La Jolla, Calif., USA). Oligonucleotides were synthesized by Biosource International (Camarillo, Calif., USA). Kit for plasmid DNA extraction from agarose gel was purchased from Qiagen (Valencia, Calif., USA).

Construction of Plasmid pUC19Tc

It was aimed to construct a positive selection vector carrying the origin of replication of the high copy number plasmid pUC19. The vector should also contain an M13 or f1 origin of replication for producing single-stranded form of DNA after co-infection with a helper phage. Furthermore, the vector should carry a phage promoter around the cloning site for easy in vitro generation of RNA probes of the insert DNA. It was decided to use an antibiotic resistance gene, such as the tetracycline resistance gene as the reporter gene in the final positive selection vector. Hence it was decided to clone the tetracycline resistance gene from pBR322 into pUC19. The ampicillin resistance gene in pUC19 would serve as the selectable marker gene.

The following forward and reverse PCR primers were synthesized:
Forward primer PUC681F:
5'-GTC GCA AGA TCT TGA AAG CTT GCG CTC TTC CGC TTC CTC GCT CAC-3' (45 bases)
Reverse primer REM1R:
5'-CCG CTC CCG GGC CTT TGC GGC CGC TTG ACA GTC GGT CCG CGG TTT CGT ATA ATG GTT CGG TGG TGT TGC TTA AGG AAG AGT ATG AGT ATT CAA C-3' (94 bases)
Forward primer REM2F:
5'-CAA GCG GCC GCA CTG CAG GTT GAC AAA GGC CAA AAA GGC CAA TAT AAT AGA GCT CAC AGA CCA CAG CCA AAG GAA CCG ACC ATG AAA TCT AAC AAT GCG CTC ATC-3' (105 bases)
Reverse primer PBR1380R:
5'-CTG AGC AGA TCT TAA TCT AGA GTT CTG CCA AGG GTT GGT TTG CGC-3' (45 bases)

The PCR primers PUC681F and REM1R would amplify the desired part of pUC19 carrying the origin of replication and the ampicillin resistance gene, whereas, the primers REM2F and PBR1380R would amplify the desired region of the tetracycline resistance gene. Appropriate restriction digestion followed by ligation of these two fragments would generate the desired plasmid, which will carry the ampicillin and tetracycline resistance genes as well as the pUC origin of replication.

The forward primer PUC681F carries the restriction sites Bgl II and Hind III at its 5' end. The reverse primer REM1R carries Not I and Sac II sites at its 5' end. These two primers will amplify the desired pUC fragment. Similarly, the forward primer REM2F carries the restriction sites Not I, Pst I, Sfi I and Sac I at its 5' end, whereas, the reverse primer PBR1380R carries Bgl II and Xba I restriction sites at its 5' end. Thus Bgl II and Not I codigestion followed by ligation of these two fragments would give the desired plasmid. The primers REM2F and REM1R carries functional regulatory elements for the ampicillin and tetracycline resistance genes, which would allow expression of both genes thus making the plasmid resistant to both antibiotics. Thus the resultant plasmid will be equivalent to pBR322 with respect to antibiotic resistance, however, it will have the pUC origin of replication giving higher copy number in E. coli.

For amplification of the pUC19 fragment the PCR conditions were:
2.5 ng pUC19 DNA
10 µM forward primer PUC681F
10 µM reverse primer REM1R
0.2 mM dNTPs (equimolar mixture of DATP, dGTP, dCTP and dTTP)
5 µl of 10× low salt buffer for Taqplus DNA polymerase
2.5 µl of 50 mM MgCl$_2$
2.5 U Taqplus DNA polymerase (Stratagene, La Jolla, Calif., USA)
Distilled water making total volume up to 50 µl.
The PCR cycle conditions were as follows:
2 min at 94° C., then 20 cycles with: 1 min at 94° C., 1 min at 55° C., 5 min at 72° C.; followed by a final extension step of 10 min at 72° C.

For amplification of the tetracycline resistance gene from pBR322 the PCR conditions were:
2.5 ng pBR322 DNA
10 µM forward primer REM2F
10 µM reverse primer PBR1380R
0.2 mM dNTPs (equimolar mixture of dATP, dGTP, dCTP and dTTP)
5 µl of 10× low salt buffer for Taqplus DNA polymerase
2.5 µl of 50 mM MgCl$_2$
2.5 U Taqplus DNA polymerase
Distilled water making total volume up to 50 µl.
The PCR cycle conditions were as follows:
2 min at 94° C., then 20 cycles with: 1 min at 94° C., 1 min at 55° C., 5 min at 72° C.; followed by a final extension step of 10 min at 72° C.

To verify the PCR reaction, 5 µl of the PCR product was electrophoresed in 0.8% agarose (Life Technologies/GIBCO-BRL, Rockville, Md., USA) gel in presence of ethidium bromide (Sigma, St. Louis, Mo., USA) for about 1 hr, and the gel was then photographed under UV light using Polaroid Type 667 films (Fisher Scientific, Suwanee, Ga., USA). The rest of the PCR-amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 50 µl of 1× appropriate restriction buffer and then incubated in presence of 20 U of Bgl II and 20 U of Not I restriction endonucleases for 1 hr at 37° C. The digested DNA was electrophoresed in 0.8% agarose gel. The desired DNA bands were excised and DNA was purified using Qiaex kit (Qiagen). The purified DNA fragments were dissolved in 30 µl of water and then used in ligation as per conditions given below:
15 µl of purified DNA fragments
4 µl of 5× ligation buffer
1 µl (5 U) of T4 DNA ligase (Life Technologies/GIBCO-BRL, Rockville, Md., USA)
Ligation was performed for overnight at 16° C.

Figure 1:
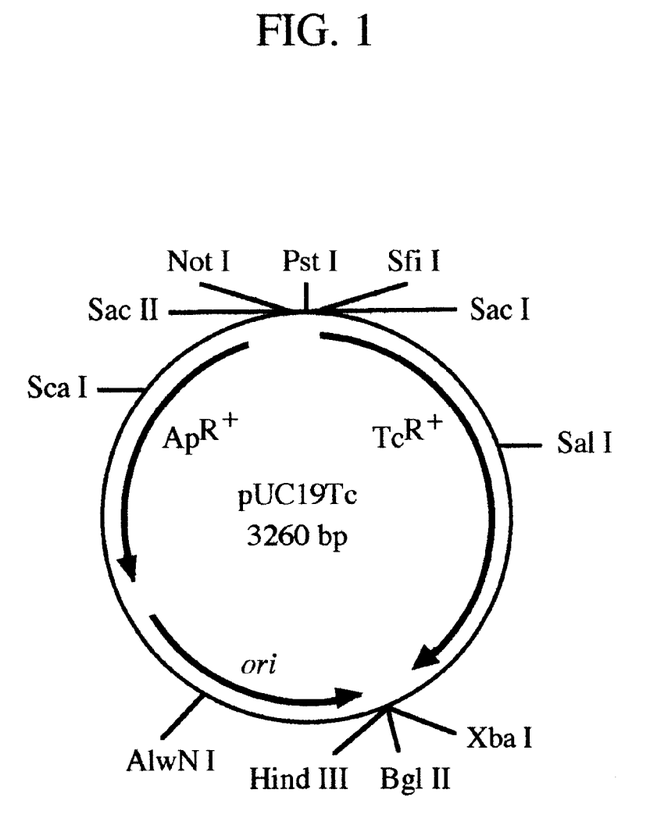
FIG. 1 shows the restriction map of plasmid pUC19Tc.

An aliquot of 2 µl ligation mix was used to transform 50 µl competent Maxefficiency DH5α (Life Technologies/GIBCO-BRL, Rockville, Md., USA) E. coli host cells according to the recommended protocols. The transformants were then plated onto LB agar plates containing 100 µg/ml ampicillin and 12.5 µg/ml tetracycline and incubated at 37° C. overnight. Some transformant colonies were individually grown in 5 ml aliquot of LB broth containing 100 µg/ml ampicillin and 12.5 µg/ml tetracycline. Small scale plasmid DNA was isolated from each individual clone, and DNA was then codigested with 20 U Bgl II and 20 U of Not I restriction endonucleases. Any plasmid DNA carrying the Bgl II and Not I cleavage sites was further characterized for the presence of other expected restriction endonuclease cleavage sites. One such plasmid carrying expected restriction endonuclease cleavage sites was named as pUC19Tc and the restriction map of this vector is shown in FIG. 1.

Construction of pUC19M13Tc

It was decided to add the M13 origin of replication to pUC19Tc which would allow production of single-stranded form of DNA after co-infection with a helper phage. The following forward PCR primer PUC119.500F and reverse primer PUC119.980R were synthesized to amplify the M13 origin region from pUC119 (Vieira and Messing, 1987, Methods Enzymol. 153, 3–11).
Forward primer PUC 119.500F:
5'-GGA AGA TCT AAG CTT ACG TCA AAG CAA CCA TAG TAC GCG CCC-3' (42 bases)

Reverse primer PUC 119.980R:
5'-GGA AGA TCT CCA TAA AAT TGT AAA CGT TAA TAT TTT GTT AAA ATT CGC-3' (48 bases)

The forward primer PUC119.500F carries the restriction sites Bgl II and Hind III at its 5' end. The reverse primer PUC119.980R also carries a Bgl II restriction site at its 5' end. Ligation of the Bgl II digested PCR product and pUC19Tc would generate the desired plasmid.

The PCR conditions were:
34.5 ng pUC119 DNA
1 μM forward primer PUC119.500F
1 μM reverse primer PUC119.980R
0.2 mM dNTPs (equimolar mixture of DATP, dGTP, dCTP and dTTP)
5 μl of 10× low salt buffer for Taqplus DNA polymerase.
2.5 μl of 50 mM $MgCl_2$
2.5 U Pfu DNA polymerase (Stratagene, La Jolla, Calif., USA)
Distilled water making total volume up to 50 μl.

The PCR cycle conditions were as follows:
2 min at 94° C., then 15 cycles with: 30 sec at 94° C., 30 sec at 55° C., 1 min at 72° C.; followed by a final extension step of 5 min at 72° C.

To verify the PCR reaction, 5 μl of the PCR product was electrophoresed in 1.5% agarose gel in presence of ethidium bromide for about 1 hr, and the gel was then photographed under UV light using Polaroid Type 667 films. The rest of the PCR-amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 25 μl of 1× Bgl II restriction buffer and then incubated in presence of 20 U of Bgl II restriction endonuclease (New England Biolabs) for 1 hr at 37° C. The digested DNA was electrophoresed in 1.5% agarose gel. The desired DNA band was excised and DNA was purified using Qiaex kit. The purified DNA was dissolved in 30 μl of water and then used in ligation. One μg of the plasmid pUC19Tc was also digested with Bgl II and DNA was treated with phenol:chloroform:isoamyl alcohol (25:24:1) and was then precipitated by ethanol. Precipitated DNA was pelleted by centrifugation and the pellet was dried in air, dissolved in 50 μl water and then used in ligation in conjunction with the purified PCR product. The conditions of ligation are given below.

10 μl of purified PCR DNA
5 μl of pUC19Tc DNA
4 μl of 5× ligation buffer
1 μl (5 U) of T4 DNA ligase Ligation was performed for overnight at 16° C.

Figure 2:
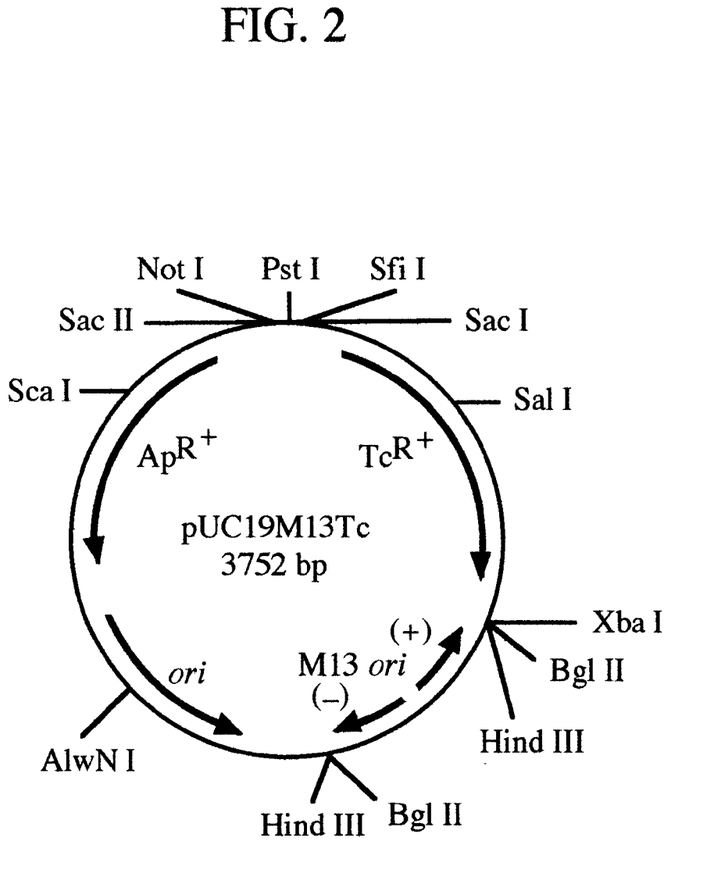
FIG. 2 shows the restriction map of plasmid pUC19M13Tc

An aliquot of 2 μl ligation Mix was used to transform 50 μl competent Maxefficiency DH5α E. coli host cells according to the recommended protocols. The transformants were then plated onto LB agar plates containing 100 μg/ml ampicillin and 12.5 μg/ml tetracycline and incubated at 37° C. overnight. Some transformant colonies were individually grown in 5 ml aliquot of LB broth containing 100 μg/ml ampicillin and 12.5 μg/ml tetracycline. Small scale plasmid DNA was isolated from each individual clone, and DNA was then digested with 20 U Bgl II restriction endonuclease. Any plasmid DNA carrying a 480 bp Bgl II fragment was further characterized for the presence of other expected restriction endonuclease cleavage sites. One such plasmid carrying all the expected restriction endonuclease cleavage sites was named as pUC19M13Tc and the restriction map of this vector is shown in FIG. 2. When infected with M13mp19 the single-stranded form of pUC19M13Tc was obtained.

Construction of the Positive Selection Vector pREM5Tc

It was decided to construct a positive selection vector based on reconstruction of a regulatory element of a reporter gene. Thus it was decided to replace the small Sac II and Sac I fragment of the vector pUC19M13Tc with an appropriate adaptor carrying regulatory elements so that the tetracycline resistance gene will serve as the reporter gene and the ampicillin resistance gene will serve as the selectable marker gene. The ampicillin resistance gene resistance promoter carries consensus −10 and −35 regions of its promoter, whereas, the tetracycline resistance gene carries only the consensus −10 region. A unique Sma I cloning site (5'-CCCGGG-3') is situated upstream of the −10 region of tetracycline resistance gene promoter such that the symmetry of the axis of the palindrome of the sequence 5'-CCCGGG-3' is just 17 bp upstream of the −10 region. The resultant plasmid will be the desired positive selection vector. The strategy of adaptor ligation was used for constructing the vector. The following complementary oligonucleotides were synthesized to generate the adaptor.

The antisense oligo REM5F:
5'-GGA AAT TAT AAA GGC CAA AGC GGC CGC TGT CAA ACC CGG GAA CAA GAA GAC AAA TAT AAT ACT ATA GTG AGT CGT ATT AGG CCA AAG CGG CCG CGA GCT-3' (99 bases)

The sense oligo REM5R:
5'-CGC GGC CGC TTT GGC CTA ATA CGA CTC ACT ATA GTA TTA TAT TTG TCT TCT TGT TCC CGG GTT TGA CAG CGG CCG CTT TGG CCT TTA TAA TTT CCG C-3' (97 bases)

The antisense and sense oligos were mixed to a final concentration of 1 pm/μl each in presence of 10 mM NaCl. The oligos were treated at 65° C. for 30 min, and then cooled down to room temperature. The resultant adaptor was used in ligation.

One μg of pUC19M13Tc DNA was dissolved in 50 μl of Sac II restriction buffer and then incubated in presence of 20 U of Sac II and 20 U of Sac I restriction endonucleases for 1 hr at 37° C. The digested DNA was electrophoresed in 0.8% agarose gel. The desired larger DNA band was excised and DNA was purified using Qiaex kit The purified DNA fragment was dissolved in 50 μl of water and then used in adaptor ligation as per conditions given below:

14 μl of purified DNA fragment
1 μl of the adaptor (REM5F and REM5R mixture)
4 μl of 5× ligation buffer
1 μl (5 U) of T4 DNA ligase Ligation was performed for overnight at 16° C.

Figure 3:
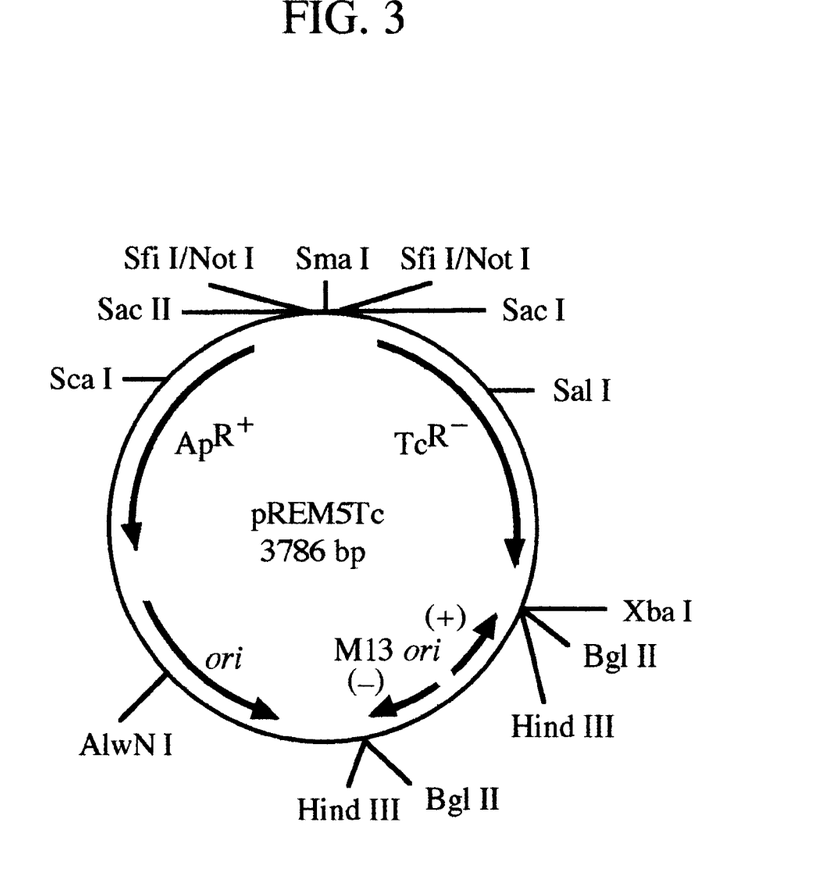
FIG. 3 shows an exemplary positive selection vector pREM5TC (Deposit No. PTA-4763, accorded a deposit date of Oct. 16, 2002, and deposited at the American Type Culture Collection, 10801 University Blvd., Manassas, VA. 20110–2209 U.S.A.) constructed according to the principle of regulatory element modulation. The tetracycline resistance reporter gene is inactive in pREM5Tc due to mutations in the −35 region of its promoter.

An aliquot of 2 μl ligation mix was used to transform 50 μl competent Maxefficiency DH5α E. coli host cells according to the recommended protocols. The transformants were then plated onto LB agar plates containing 100 μg/ml ampicillin and incubated at 37° C. overnight. Some transformant colonies were individually transferred to LB agar plates containing 100 μg/ml ampicillin as well as to LB agar plates containing 12.5 μg/ml tetracycline. The clones sensitive to tetracycline were then individually grown in 5 ml aliquot of LB broth containing 100 μg/ml ampicillin. Small scale plasmid DNA was isolated from each individual clone, and DNA was then digested with 20 U Sma I restriction endonuclease. Any plasmid DNA carrying a Sma I cleavage site was further characterized for the presence of other expected restriction endonuclease cleavage sites. One such plasmid carrying all the expected restriction endonuclease cleavage sites was named as pREM5Tc and the restriction map of this vector is shown in FIG. 3. The vector pREM5Tc is sensitive to tetracycline and resistant to ampicillin. FIG. 4 shows the DNA sequence indicating the Sma I cloning site, T7 phage promoter sequence, and other related restriction sites in pREM5Tc.

Large scale DNA of pREM5Tc was prepared using plasmid Maxiprep kit from Qiagen. An aliquot of 2 µg of pREM5Tc DNA was digested with 20 U of Sma I restriction endonuclease for 1 hr at 25° C. The digest was then incubated at 70° C. for 30 min to inactivate Sma I, and was diluted with sterile DEPC-treated water to give final concentration 50 ng/µl. The vector pREM5Tc thus prepared was tested for direct cloning of PCR products as well as for its capability as a positive selection vector.

Example of Direct Cloning of PCR Product into pREM5Tc

The vector pREM5Tc has the potential to clone any DNA fragment carrying an independently functional promoter. Hence it was decided to clone a PCR fragment which does not carry any known promoter.

A promoterless 420 bp fragment of the lacZ was separately PCR-amplified using Taq DNA polymerase (without 3'-5' proof reading exonuclease activity) and Pfu DNA polymerase (with 3'-5' proof reading exonuclease activity).

Following are the primers used in amplification of the above mentioned 420 bp DNA fragment:
Forward primer LC1261REM5F:
5'-TGT CAA GCT TAC AAT TTC ACA CAG GAA ACA GCT ATG-3' (36 bases)
Reverse primer LC1680R:
5'-TTT CAT CAA CAT TAA ATG TGA GCG AGT AAC-3' (30 bases)

The forward primer LC1261REM5F carries 5-TGTCAA-3' at its 5' end as well as a Hind III site for elucidation of orientation of the insert in the recombinant plasmid. The vector pREM5Tc carries two Hind III sites.

The PCR conditions were:

1 µg E.coli DNA

10 µM forward primer (LC1261REM5F)

10 µM reverse primer (LC1680R)

0.2 mM dNTPs (equimolar mixture of dATP, dGTP, dCTP and dTTP)

5 µl of 10× buffer for Taq or Pfu DNA polymerase 2.5 U Taq or Pfu DNA polymerase Distilled water making total volume up to 50 µl.

The PCR cycle conditions were as follows:

2 min at 94° C., then 25 cycles with: 1 min at 94° C., 1 min at 55° C., 1 min at 72° C.; followed by a final extension step of 5 min at 72° C.

To verify the PCR reaction, 5 µl of the PCR product was electrophoresed in 1.5% agarose gel in presence of ethidium bromide for about 1 hr, and the gel was then photographed under UV light using Polaroid Type 667 films.

Ligation was performed using 1–200 ng of Sma I digested pREM5Tc vector DNA, and 1–5 µl of the PCR product The conditions of a typical ligation experiment is given below:

1 µl (50 ng) of Sma I digested vector pREM5Tc DNA

2 µl (200 ng) of PCR product

4 µl of 5× ligase buffer

12 µl of DEPC-treated water

1 µl (5 U) of T4 DNA ligase

Ligation mixture was incubated at room temperature for 5–30 min or at 16° C. for overnight.

Different amounts (2–10 µl) of ligation mix were used to transform 10–100 µl of competent Maxefficiency DH5α E. coli cells. In a typical transformation 50 µl of DH5α was transformed with 2 µl of ligation mixture for 30 min on ice, followed by heat shock at 42° C. for 50 sec, 2 min on ice, addition of 1.0 ml of SOC medium (Life Technologies/GIBCO-BRL, Rockville, Md., USA), and incubation at 37° C. for 1 hr. The transformants were spun down, resuspended in 50 µl of SOC medium and then plated onto LB agar plates containing 100 µl ampicillin and 12.5 µg/ml tetracycline and incubated overnight at 37° C. As expected, control ligation sample of vector alone gave only a few transformants, whereas, ligation samples of vector plus PCR fragments gave many transformant colonies. Some transformant clones were individually cultured in 5 ml LB broth containing 100 µg/ml ampicillin and 12.5 µg/ml tetracycline for overnight at 37° C. Small scale plasmid DNA was isolated using standard alkaline lysis method (Sambrook et al., Molecular Cloning: A Laboratory Manual, Cold Spring Harbor Laboratory, Cold Spring Harbor, N.Y., 1989). The isolated plasmid DNA was characterized by Not I or Sfi I restriction endonuclease digestion. The result of a typical cloning experiment is shown in Table 1.

TABLE 1

| pREM5Tc[a] (vector used in ligation) | PCR fragment (polymerase used) | colonies/ml transformation mix | positive clones/ analyzed clones[c] |
|---|---|---|---|
| 50 ng | 2 µl (Taq DNA polymerase) | 425 | 9/9 |
| 50 ng | 2 µl (Pfu DNA polymerase) | 1240 | 9/9 |
| 50 ng | — | 4 | — |

[a]The positive selection vector pREM5Tc was digested with Sma I restriction enzyme, and after heat inactivation of Sma I the vector DNA was used in ligation.
[b]Transformants were grown in presence of 100 µg/ml ampicillin and 12.5 µg/ml tetracycline.
[c]The plasmids from the transformants were digested with either Not I or Sfi I releasing the insert.

As expected, the Table 1 shows that the vector pREM5Tc is capable of cloning the PCR fragments carrying 5'-TGTCAA-3' at its 5' end as produced by primers LC1261REM5F and LC1680R. The PCR fragment carries a 5'-TTGACA-3' at its 3' end, which is complementary to the 5'-TGTCAA-3' sequence in the primer LC1261REM5F. The 5'-TTGACA-3' sequence serves as the consensus −35 region for an E. coli promoter. Table 1 also shows that the vector pREM5Tc is capable of cloning both types of PCR products produced by Taq and Pfu DNA polymerases. However, fewer number of clones are obtained in case of cloning of the PCR products obtained by Taq DNA polymerase because in such case only those PCR products of Taq DNA polymerase are ligated which have no dAMP overhang. Improved efficiency of cloning of the PCR products generated with Taq DNA polymerase could be achieved by treating the PCR products with a DNA polymerase with 3'-5' proof-reading exonuclease activity (T4 DNA polymerase, Pfu DNA polymerase etc.) thus removing the overhang dAMP (Costa and Weiner, 1994, Nucl. Acids Res. 22, 2423). The result also shows that 100% of the analyzed clones carried the 420 bp insert, which confirms the positive selection capability of the vector pREM5Tc. Analysis of the Hind III restriction digestion products of the transformants proved that inserts in all transformants were also cloned unidirectionally such that 5'-TTGACA-3' was proximal to the Sac I restriction site, which indicates that 5'-TTGACA-3' was the functional −35 region for the tetracycline resistance gene in the recombinant transformants.

Use of pREM5Tc Eliminates False Positive Clones

A positive selection vector developed based on reconstruction of a regulatory element should greatly reduce, if not eliminate, generation of false positive clones. Thus pREM5Tc was tested for its capability of eliminating false positive clones in a cloning experiment. An aliquot of 1 μg of the vector pREM5Tc was digested with 20 U of Sma I for 1 hr and another aliquot of 1 μg of the vector pREM5Tc was digested with 100 U of Sma I for 4 hr at 25° C. Similarly, An aliquot of 1 μg of the vector pUC19 was digested with 20 U of Sma I for 1 hr and another aliquot of 1 μg of the vector pUC19 was digested with 100 U of Sma I for 4 hr at 25° C. The digests were treated at 70° C. for 30 min to inactivate the restriction endonucleases. The digested vectors were then diluted with water (10 ng/μl) and recircularized by ligation, the conditions of which are given below:

1 μl (10 ng) of vector DNA
4 μl of 5× ligase buffer
14 μl of DEPC-treated water
1 μl (5 U) of T4 DNA ligase Ligation mixture was incubated at 16° C. for overnight.

An aliquot of 2 μl of ligation mix was used to transform 50 μl of competent Maxefficiency DH5α E. coli cells for 30 min on ice, followed by heat shock at 42° C. for 50 sec, 2 min on ice, addition of 1.0 ml of SOC medium, and incubation at 37° C. for 1 hr. For the pUC19 derivatives, an aliquot of 50 μl of the transformation mix was plated onto LB agar plates containing 100 μg/ml ampicillin, 100 ng/ml X-gal and 1 mM IPTG and incubated overnight at 37° C. For the pREM5Tc derivatives, cells from 1 ml transformation mix were spun down, resuspended in 50 μl of S.O.C. medium, and was then plated onto LB agar plates containing 100 μg/ml ampicillin and 12.5 μg/ml tetracycline and incubated overnight at 37° C. In case of pUC19 derivatives, all white colonies were considered false positive clones, whereas, the blue colonies were considered wild-type clones. In case of pREM5Tc derivatives, all clones were considered false positive clones. Table 2 shows the effect of exonuclease digestion for generating false positive clones in a cloning experiment.

TABLE 2

| Vector used in ligation[a] | Amount of DNA (μg) | Units of Sma I | Period of incubation (h) | Colonies/ml transformation mix[b] | False positive clones[c] |
|---|---|---|---|---|---|
| pREM5Tc | 1 | 20 | 1 | 1 | 1 |
| pREM5Tc | 1 | 100 | 4 | 0 | 0 |
| pUC19 | 1 | 20 | 1 | 90,000 | 4,400 |
| pUC19 | 1 | 100 | 4 | 36,000 | 17,000 |

[a]The positive selection vector pREM5Tc and the chromogenic selection vector pUC19 were separately digested with Sma I restriction enzyme, and after heat inactivation of Sma I each digest (10 ng) was subjected to self-ligation.
[b]For pREM5Tc derivatives, transformants were grown in presence of 100 μg/ml ampicillin and 12.5 μg/ml tetracycline, whereas, for pUC19 derivatives, transformants were grown in presence of 100 μg/ml ampicillin.
[c]In case of pREM5Tc derivatives, all colonies were considered false positive clones. In case of pUC19 derivatives, all white colonies were considered false positive clones, whereas, the blue colonies were considered wild-type clones.

It is evident form the data in Table 2 that contaminating exonuclease greatly increases the number of false positive clones in case of pUC19, wherein the cloning site in pUC19 is in the chromogenic lacZ gene. The possibility of these false positive clones arising from spontaneous mutations or from post-transformation deletion and recircularization of the vectors, were considered unlikely, because in such case the number of false positive clones should have been similar for both time periods. This result also shows that exonuclease has no effect on generating false positive clones in case of pREM5Tc and use of pREM5Tc practically eliminates false positive clones in a cloning experiment.

In conclusion, a strategy for developing a positive selection vector system based on regulatory element modulation has been established; and wherein a vector pREM5Tc thus developed has been successfully used for direct cloning of PCR-generated DNA fragments. Use of pREM5Tc also eliminates exonuclease-induced false positive clones in a cloning experiment.

I claim:
1. A vector comprising:
 (a) an origin of replication;
 (b) a selectable marker gene;
 (c) a reporter gene;
 (d) a functionally inactive, insertionally reconstructable promoter; and
 (e) a cloning site,
 wherein the functionally inactive, insertionally reconstructable promoter is positioned to regulate expression of the reporter gene when said functionally inactive, insertionally reconstructable promoter is reconstructed by insertion of a suitable nucleic acid.
2. A vector as claimed in claim 1, wherein the origin of replication is selected from the group consisting of:
 (a) a prokaryotic origin of replication;
 (b) an eukaryotic origin of replication;
 (c) a viral origin of replication;
 (d) plasmid pUC;
 (e) plasmid pBR322;
 (f) phage M13;
 (g) phage f1; and
 (h) a combination thereof.
3. A vector as claimed in claim 1, wherein the selectable marker gene is selected from the group consisting of:
 (a) an antibiotic resistance gene;
 (b) a gene that is essential for growth of the host;
 (c) an essential gene for replication and propagation of the vector in the host cell;
 (d) a gene for encoding a chromogenic protein;
 (e) a gene encoding a fluorescent protein; and
 (f) a combination thereof.
4. A vector as claimed in claim 1, wherein the reporter gene is selected from the group consisting of:
 (a) an antibiotic resistance gene
 (b) an essential gene for the growth of the host;
 (c) an essential gene for replication and propagation of the vector in the host cell;
 (d) a toxic gene;
 (e) a gene encoding a chromogenic protein;
 (f) a fluorescent protein gene; and
 (g) a combination thereof.
5. A vector as claimed in claim 1, wherein the regulatory gene is selected from the group consisting of:
 (a) a positive regulatory gene; and
 (b) a negative regulatory gene.
6. A vector of any of claims 1, wherein the promoter comprises:
 (a) a −35 region of an E. coli promoter or a prokaryotic equivalent to the −35 region of an E. coli promoter;
 (b) a −10 region of an E. coli promoter or a prokaryotic equivalent to the −10 region of an E. coli promoter; and

(c) a spacer region between the −10 and −35 regions or a prokaryotic equivalent to the spacer region between the −10 and −35 regions.

7. A vector as claimed in claim 1, wherein the cloning site is selected from the group consisting of:
(a) a restriction enzyme cleavage site that is unique in said vector;
(b) multiple restriction sites;
(c) a restriction enzyme cleavage site that is not unique in said vector; and
(d) a combination thereof.

8. A vector as claimed in claim 1, wherein said vector further comprises a promoter selected from the group consisting of:
(a) a phage promoter;
(b) a viral promoter;
(c) a T7 promoter,
(d) a T3 promoter;
(e) an SP6 promoter;
(f) a prokaryotic promoter;
(g) an eukaryotic promoter;
(h) a combination thereof; and
wherein the promoter is positioned around the cloning site.

9. A vector as claimed in claim 1, wherein the vector further comprises one or more additional genes selected from the group consisting of: a reporter gene and a regulatory gene.

10. A vector pREM5Tc, as present in ATCC Deposit No. PTA-4763.

11. A vector as claimed in claim 1, wherein such a vector is used for any or a combination of the following:
(a) cloning a DNA fragment generated by polymerase chain reaction (PCR);
(b) cloning an appropriate restriction DNA fragment;
(c) cloning an appropriate DNA fragment;
(d) diagnostic cloning;
(e) protein production; and
(f) gene therapy.

12. A vector comprising:
(a) an origin of replication;
(b) a selectable marker gene;
(c) a reporter gene;
(d) a functional promoter; and
(e) a cloning site,
wherein the cloning site is positioned such that insertion of a nucleic acid at the cloning site results in a functionally inactive promoter.

13. A vector comprising:
(a) an origin of replication;
(b) a selectable marker gene;
(c) a reporter gene;
(d) a functional promoter;
(e) a regulatory gene;
(f) a functionally inactive, insertionally reconstructable promoter; and
(g) a cloning site,
wherein the functional promoter regulates expression of the reporter gene, and wherein the functionally inactive, insertionally reconstructable promoter is positioned to regulate expression of the regulatory gene when the functionally inactive, insertionally reconstructable promoter is reconstructed by insertion of a suitable nucleic acid, and wherein a gene product of the regulatory gene regulates the functional promoter.

14. A vector comprising:
(a) an origin of replication;
(b) selectable marker gene;
(c) a reporter gene;
(d) a first promoter that is a functional promoter;
(e) a regulatory gene;
(f) a second promoter that is a functional promoter; and
(g) a cloning site,
wherein the first promoter regulates expression of the reporter gene, and wherein the second promoter regulates expression of the regulatory gene, and wherein a gene product of the regulatory gene regulates the first promoter, and wherein insertion of a nucleic acid at the cloning site destroys the function of the second functional promoter.

15. A kit comprising a vector of any of claims 1, 10, 12, 13, or 14 and further comprising one or more components selected from the group consisting of:
(a) an adaptor carrying a promoter or part thereof;
(b) a linker carrying a promoter or part thereof;
(c) DNA ligase;
(d) T4 DNA polymerase;
(e) T4 polynucleotide kinase;
(f) dNTPs;
(g) compatible competent host cells;
(h) a control target DNA, wherein the control target DNA is used for control PCR, the product of which is then ligated into the vector;
(i) a forward control primer;
(j) a reverse control primer;
(k) a non-linearized control plasmid.

16. The kit of claim 15, wherein the vector is linearized.

17. A vector comprising:
(a) a pUC origin of replication;
(b) an M13 origin of replication;
(c) an ampicillin resistance gene operably linked to a functional promoter;
(d) a tetracycline resistance gene linked to a non-functional promoter, wherein the non-functional promoter comprises a functional −10 promoter sequence but not a −35 promoter sequence;
(e) a unique SmaI cloning site having the sequence 5'CCCGGG-3', wherein the SmaI cloning site is positioned such that upon digestion and ligation with a nucleic acid having a correct −35 sequence at its 3' end, the non-functional promoter is reconstructed to promote expression of the tetracycline resistance gene; and
(f) a T7 phage promoter located downstream of the cloning site.

18. A vector as claimed in claim 1, 10, 13, or 17, wherein the vector decreases the frequency of false positives when used for cloning.

19. A method for using a vector of claim 1 or 13, the method comprising inserting a nucleic acid at a cloning site of a vector of claim 1 or 13, wherein inserting the nucleic acid reconstructs the functionally inactive, insertionally reconstructable promoter.

20. The method of claim 19, wherein inserting the nucleic acid comprises using a reagent selected from the group consisting of:

(a) a ligase;

(b) a recombinase;

(c) a topoisomerase;

(d) an adaptor;

(e) a linker; and (f) a combination thereof.

21. A PCR primer comprising a nucleic acid sequence selected from the group consisting of:

(a) a functional promoter;

(b) multiple functional promoters;

(c) a part of a promoter; and (d) multiple parts of a promoter, wherein the nucleic acid sequence, upon ligation with a vector of claim 1, 10, 13 or 17 functions as an active promoter and/or reconstructs a functionally active, insertionally reconstructable promoter.

22. A PCR primer of claim 21, wherein the PCR primer comprises the sequence 5'-TGTCAA-3' at its 5' end.

* * * * *